United States Patent [19]
Reddick et al.

[11] Patent Number: 5,468,486
[45] Date of Patent: Nov. 21, 1995

[54] VACCINE CONTAINING A PROTEIN ALKALOID CONJUGATE FOR THE TREATMENT OF FESCUE TOXICOSIS

[75] Inventors: Bradford B. Reddick; Kimberly D. Gwinn; Jack W. Oliver, all of Knoxville, Tenn.

[73] Assignee: The University of Tennessee Research Corporation, Knoxville, Tenn.

[21] Appl. No.: 205,194

[22] Filed: Mar. 3, 1994

Related U.S. Application Data

[63] Continuation of Ser. No. 823,146, Jan. 21, 1992, abandoned.

[51] Int. Cl.[6] .................... A61K 39/385; A61K 39/00; C07K 14/37; C07K 14/765
[52] U.S. Cl. .................... 424/194.1; 424/274.1; 435/964; 436/543; 436/816; 530/363; 530/367; 530/404; 530/405; 530/406; 530/408; 530/409; 530/410
[58] Field of Search .................... 424/88, 274.1, 424/194.1; 435/254, 964; 530/403, 363, 367, 404–406, 408–410

[56] References Cited

U.S. PATENT DOCUMENTS

| | | | |
|---|---|---|---|
| 3,822,245 | 7/1974 | Spector et al. | 530/389.8 |
| 3,849,562 | 11/1974 | Richardson | 514/288 |
| 4,659,715 | 4/1987 | Meier et al. | 514/288 |
| 4,755,519 | 7/1988 | Dougherty et al. | 514/276 |
| 4,847,243 | 7/1989 | Wallace | 514/30 |
| 4,880,632 | 11/1989 | Lipham et al. | 424/425 |
| 4,965,272 | 10/1990 | Hufford et al. | 514/288 |

OTHER PUBLICATIONS

Savary et al. Phytopathology 80:1052–1054 1990.
Shelby et al. J. Agric. Food Chem 38:1130–1134 1990.
Shelby et al. Food Agric. Immunol. 3:169–177 1991.
Lyons, P. C. et al. Science 232:487–489 1986.
Solomons, R. N. et al. Am. J. Vet. Res. 50:235–236 1989.
Thompson et al. Proceedings of 2d Int. Symp. on Aeremonium/Grass Interactions, pp. 135–137, 1993.
Chanh, et al.—J. Immunol. 144(12), 1990.

*Primary Examiner*—Mary E. Mosher
*Assistant Examiner*—Anthony C. Caputa
*Attorney, Agent, or Firm*—Weiser & Associates

[57] ABSTRACT

A method for the treatment of the symptoms of fescue toxicosis in mammals comprising injecting a subject mammal with a vaccine which includes from about 5 µg to about 1 mg of a protein-alkaloid conjugate per mL of a physiologically acceptable carrier. There is also provided a vaccine for the treatment of the symptoms of fescue toxicosis and a compound for preparing that vaccine.

6 Claims, No Drawings

VACCINE CONTAINING A PROTEIN ALKALOID CONJUGATE FOR THE TREATMENT OF FESCUE TOXICOSIS

This is a continuation of application Ser. No. 07/823,146, filed Jan. 21, 1992 now abandoned.

FIELD OF THE INVENTION

The field of the present invention is related to the areas of veterinary medicine and animal science, and particularly a method for the treatment of the symptoms of fescue toxicosis.

BACKGROUND OF THE INVENTION

Fescue forage is a major nutritional source for cattle in the United States, especially in the Eastern sector. The fungus *Acremonium coenophialum* that is endemic to fescue and considered a symbiont produces ergopeptide and other alkaloids that are causally related to inferior production and health in cattle via ill-defined mechanisms involving metabolism and/or nutrient intake. As a result, growth rate and milk production are decreased and reproductive problems occur in animals that are fed endophyte-infected fescue. According to the results of a 1990 national survey of twenty-one tall fescue-growing states with twenty-five million acres of tall fescue, the alkaloid toxicity associated with the intake of fungus-infested fescue currently results in an estimated 609 million dollar annual loss to the cattle industry. Elimination of the fungus from fescue is both impractical and undesirable because the alkaloids produced by this fungus afford increased heartiness to plants by increasing drought and pest resistance. An alternative to the elimination of the fungus from fescue grass is to prevent the effects of the toxic-fungal alkaloids with either chemotherapeutic agents or a vaccine for the prophylaxis of this major production-limiting disease in cattle and horses.

The use of chemotherapeutic agents to treat the effects of the toxic-fungal alkaloids requires a continued investment in time and money for those involved in raising cattle and horses on fescue forage. An effective vaccine to toxic-fescue alkaloids has several advantages over the use of chemotherapeutic agents. Vaccines are relatively easy to administer using one or a few injections; vaccines are more economical than the continuous treatments required with chemotherapeutic agents; and vaccines have a smaller potential for residue problems. Thus, there would be significant economic benefit to cattle and horse producers with the availability of a successful vaccine to treat the symptoms of fescue toxicosis.

It is an object of the present invention to provide a method for the treatment of the symptoms of fescue toxicosis in mammals.

It is also an object of the present invention to provide a vaccine for treating the symptoms of fescue toxicosis in mammals.

It is a further object of the present invention to provide a protein-alkaloid conjugate for the preparation of a vaccine for treating the effects of fescue toxicosis.

SUMMARY OF THE INVENTION

The present invention provides a method for the treatment of the symptoms of fescue toxicosis in mammals comprising injecting a subject mammal with a vaccine including from about 5 µg to about 1 mg of a protein-alkaloid conjugate per mL of a physiologically acceptable carrier. In preferred embodiments of the invention, a subject mammal is injected twice, approximately one month between injections, if needed. The mammals subject to the vaccination comprise cattle and horses.

In another preferred embodiment of the invention the alkaloid of the protein-alkaloid conjugate is selected from the group consisting of ergonovine, ergonovinine, ergovaline, ergosine, β-ergosine, ergonine, ergotamine, ergoptine, β-ergoptine, ergocornine, ergostine, ergovalinine, α-ergocryptine, β-ergocryptine, ergocristine, ergosinine, βergosinine, ergoninine, ergotaminine, ergostinine, βergoptinine, ergocorninine, ergoptinine, α-ergocryptinine, βergocryptinine, ergocristinine, ergothioneine, ergotinine, ergotoxine, perloline, loline, N-acetylloline, N-formylloline, halostachine, harmane and norharmane. Further, the protein is selected from the group consisting of bovine serum albumin, keyhole limpet haemocyanin, and ovalbumin.

DETAILED DESCRIPTION OF THE INVENTION

The protein-alkaloid conjugate may be prepared by any one of a number of procedures well known in the art. For example, IMJECT IMMUNOGEN EDC conjugation kits by Pierce provide the materials and reagents necessary for producing protein-alkaloid conjugates with either bovine serum albumin, keyhole limpet haemocyanin, or ovalbumin.

The protein-alkaloid conjugate is formed in order to elicit an immune response from the vaccinated subject mammal. The alkaloid molecules themselves are too small to be recognized by mammalian immune systems and, therefore, do not produce an immune response when injected directly into the host. Instead, the host mammal exhibits the symptoms of ergot alkaloid poisoning.

A physiologically acceptable carrier for the vaccine includes distilled water, normal saline, or physiologically buffered saline. Adjuvants such as alum or vegetable oil may also be used in combination with the conjugate. An effective vaccine is produced with a concentration of the protein-alkaloid at from about 5 µg to about 1 mg per mL of the carrier. At least about 5 µg of the conjugate per mL of the carrier is required to elicit immunological response in the host mammal. More than about 1 mg of the conjugate per mL of the carrier does not provide additional protection and may subject the host mammal to undesired side effects.

The present invention also provides for a vaccine for treating a mammal for the symptoms of fescue toxicosis. The vaccine comprises a protein-alkaloid conjugate in a physiologically acceptable carrier. The concentration of the conjugate is from about 5 µg to about 1 mg per mL of the carrier. In a preferred embodiment of the invention, the ergot alkaloid of the protein-alkaloid conjugate is selected from the group consisting of ergonovine, ergonovinine, ergovaline, ergosine, βergosine, ergonine, ergotamine, ergoptine, β-ergoptine, ergocornine, ergostine, ergovalinine, α-ergocryptine, β-ergocryptine, ergocristine, ergosinine, β-ergosinine, ergoninine, ergotaminine, ergostinine β-ergostinine, ergocorninine, ergoptinine, α-ergocryptinine, β-ergocryptinine, ergocristinine, ergothioneine, ergotinine, ergotoxine, perloline, loline, N-acetylloline, N-formylloline, halostachine, harmane and norharmane. Further, in a preferred embodiment of the invention, the protein is selected from the group consisting of bovine serum albumin, keyhole limpet haemocyanin, or ovalbumin. A physiologically acceptable carrier for the vaccine includes distilled water, normal saline, and physiologically buffered saline.

In order to facilitate a further understanding of the invention, the following procedure is given primarily to illustrate certain more specific aspects of the invention.

PROCEDURE

Protein-alkaloid conjugate preparation: Twenty milligrams of ergonovine base (61.5 μmol) and 12.7 mg succinic anhydride were dissolved in 1.5 ml pyridine, flushed with a stream of $N_2$, sealed, and incubated overnight in the dark at room temperature. The pyridine was removed with $N_2$ at 37° C. and the resulting residue was dissolved in 1 ml of 0.1 $NH_4Cl$ and extracted with ethylacetate. The aqueous phase was flushed with nitrogen to remove traces of ethylacetate. The mixture was neutralized with dilute NaOH and loaded onto a preconditioned Waters C18 SEPPAK® column. The SEPPAK® column was washed with water until a fluorescent band began to elute (ca. 4 ml). The ergonovine-hemisuccinate was then eluted with 25% MeOH. The MeOH was removed under reduced pressure at 37° C. and the remaining material was lyophilized. Conjugation of ergonovine to human serum albumin (HSA) was performed by first adding 39 mg of lyophilized ergonovine-hemisuccinate to 2 ml of 18.6 mg/ml human serum albumin in 0.03M phosphate buffer (pH 7.6). Next, 1 ml of 20 mg/ml 1-ethyl-3-(3-dimethylaminopropyl)carbodiimide (Sulfo-NHS) was then added and the pH adjusted to 7.6. The preparation was allowed to mix overnight in the dark at room temperature and was then dialyzed for two days with frequent changes of deionized water. A similar procedure is followed to prepare similar protein-alkaloid conjugates using a variety of proteins (such as keyhole limpet haemocyanin (KLH) or ovalbumin) and a variety of alkaloids (such as ergovaline, ergosine or ergovinine).

Antiserum preparation: Three female New Zealand white rabbits were immunized with the HSA-ergonovine conjugate and two with the KLH-ergonovine conjugate. Initially, each rabbit was injected with 1 mg of the respective conjugate in 1 ml of phosphate buffered saline that had been emulsified with an equal amount of Freund's complete adjuvant. Booster injections of 0.2 mg of conjugate per rabbit, emulsified with Freund's incomplete adjuvant, were given at 5 and 10 weeks after the first injections. The rabbits were bled 8 and 16 days after each booster injection. Serum was collected after two cycles of low speed centrifugation. Serum from each rabbit was pooled before testing in the competitive enzyme linked immunosorbent assay (ELISA).

Competitive ELISA: Duplicate polystyrene ELISA plates were numbered and rinsed once with distilled water. The HSA-ergonovine conjugate [0.625 μl/ml in carbonate coating buffer (0.5μ sodium carbonate, pH 9.6)] was pipetted into each well (2 μl/well). After 2H at 30° C. the plates were washed 4 times quickly with physiologically buffered saline (PBS) Tween (0.02M phosphate, 0.15M NaCl, 3 mM KCl+ 0.05% TWEEN 20, pH 7.3). All subsequent rinse steps were done with PBS-Tween. Serial dilutions were made of seven compounds used in the competitive assay. All dilutions were made in PBS-Tween. These compounds and their initial concentrations were: agroclavine 0.5 mM, ergocryptine at 100 μM, unconjugated ergonovine at 1 μM, ergotamine at 100 μM, ergovaline at 10 μM, lysergol at 10 mM, dihydroergotamine at 200 μM and IAA at 1 mM. After placing 100 μl of each dilution in duplicate wells, an additional 100 μl of antiserum, produced against the ergonovine KLH conjugate, was added to each well at a dilution of 1:1000 and mixed.

The plates were incubated for 2 H at 30° C. and again rinsed 4 times quickly. Protein-A alkaline phosphatase (0.5 μg/ml in PBS-Tween) was placed in wells (200 μl/well) and incubated for 2 H at 30° C. The plates were again rinsed 4 times. Substrate, SIGMA 104® phosphatase substrate (5 mg/ml), in 10% diethanolamine, pH 9.6 was added to each well (150 μl/well). The reaction was stopped after 30 min. with 3M NaOH (75 μl/well). The plates were read on a DYNATECH MINIREADER II® reader. Mean values were calculated from duplicate wells per plate and duplicate plates were averaged. From these values a percent maximal absorbance level was calculated.

Results and discussion: Ergovaline is found in E+ fescue in higher concentrations than any other alkaloid, but is not available in quantities sufficient for antiserum production. Ergonovine, which is commercially available and structurally similar to ergovaline, was used to produce antisera for detection of ergovaline and other alkaloids in fescue forage. One antiserum, produced by a rabbit in response to injections of KLH-ergonovine conjugate, was satisfactory in the competitive ELISA tests. Results from the competitive ELISA with this antiserum are shown in Table 1. The antiserum reacted with all ergot alkaloid compounds tested, but not with IAA. Ergopeptide compounds, except for dihydroergotamine, were better competitors than the clavine compounds (Table 1). Ergonovine was more competitive in the ELISA than any of the other compounds, having a predicted concentration for 50% maximal absorbance ($A_{50}$) of 1.6 ng/ml (Table 1). Ergovaline, ergotamine, ergocrytine and agroclavine all had $A_{50}$ values below 100 ng/ml or were 2% or greater cross reactive (Table 1); therefore this antiserum could be used to detect these compounds in tissue. Lysergol and dihydroergotamine were less than 1% cross reactive and can not be easily detected with this antiserum. The antiserum could also distinguish between E+ and E− fescue in a competitive ELISA competing for antibodies.

TABLE 1

Predicted values for 50% maximal absorbance levels for various ergot alkaloids in a competitive ELISA (Linear Regression, Abstract).

| Compound | Concentration (μM) of 50% A | Slope | Concentration (ng/ml) of 50% A | Cross Reactivity (%) |
| --- | --- | --- | --- | --- |
| ergonovine | 0.05 | −26.4 | 1.6 ng/ml | 100% |
| ergovaline | 0.15 | −15.5 | 8 ng/ml | 20% |
| ergotamine | 0.40 | −16.1 | 23 ng/ml | 7% |
| ergocryptine | 0.59 | −19.7 | 33 ng/ml | 5% |
| agroclavine | 3.2 | −19.4 | 76 ng/ml | 2% |
| lysergol | 3.7 | −13.7 | 940 ng/ml | 4% |
| dihydroergotamine | 117.0 | −22.5 | 6833 ng/ml | 4% |

Bovine Isolated Blood Vessel Response to Alkaloid Antibodies: Using a bovine isolated blood vessel model, antibodies against ergonovine prevented the normal vasoconstrictor response of ergonovine. Blood vessels exposed to $10^{-7}$ molar ergonovine in isolated organ baths (10 ml) plus ergovine antibody (IgG) added to baths in concentrations of 0.00065, 0.0065, 0.065, 0.65, and 6.5 mg gave 3.4, 3.4, 3.3, 2.1, and 0.0 grams contractile response, respectively after 30 minutes incubation. Similarly, blood vessels exposed to $10^{-7}$ molar ergotamine in tissue baths with the same antibody concentrations gave 5.6, 3.4, 1.0, 0.9, and 1.4 grams contractile response, respectively, after the 30 minute incubation period. Thus, increasing amounts of the antibody gave a progressive inhibition of vasoconstriction by ergonovine and ergotamine. Therefore, the treatment of mammals, such as cattle and horses, with the protein-alkaloid conjugate will generate the antibodies necessary to prevent the symptoms of fescue toxicosis.

Thus, the present invention provides a method for the treatment of fescue toxicosis in mammals. In addition, the present invention provides a vaccine for the treatment of the symptoms of rescue toxicosis in mammals. Further, the present invention provides a protein-alkaloid conjugate for the preparation of a vaccine for the treatment of fescue toxicosis in mammals.

Various of the features of the invention which are believed to be new are set forth in the appended claims.

What is claimed is:

1. A method for the treatment of the symptoms of fescue toxicosis in cattle and horses comprising injecting a subject cow or horse with a vaccine including from about 5 µg to about 1 mg of a protein-alkaloid conjugate per mL of a pharmaceutically acceptable carrier, wherein the alkaloid of the protein-alkaloid conjugate is selected from the group consisting of ergonovine, ergonovinine, ergovaline, ergosine, β-ergosine, ergonine, ergotamine, ergoptine, β-ergoptine, ergocornine, ergostine, ergovalinine, α-ergocryptine, β-ergocryptine, ergocristine, ergosinine, β-ergosinine, ergoninine, ergotaminine, ergoptinine, β-ergoptinine, ergocorninine, ergostinine, α-ergocryptinine, β-ergocryptinine, ergocristinine, ergothioneine, ergotinine, ergotoxine, perloline, N-acetylloline, and halostachine, wherein the protein of the protein-alkaloid conjugate is selected from the group consisting of bovine serum albumin and ovalbumin, and wherein the conjugate is a carbodiimide reaction product in which said alkaloid is coupled to said protein.

2. The method of claim 1 wherein the alkaloid is ergonovine and the protein is ovalbumin.

3. The method of claim 1 wherein the alkaloid is ergonovine.

4. A vaccine for the treatment of the symptoms of fescue toxicosis in cattle and horses and for immunizing same comprising from about 5 µg to about 1 mg of a protein-alkaloid conjugate per mL of a pharmaceutically acceptable carrier, wherein the alkaloid of the protein-alkaloid conjugate is selected from the group consisting of ergonovine, ergonovinine, ergovaline, erogsine, β-ergosine, ergonine, ergotamine, ergoptine, β-ergoptine, ergocornine, ergostine, ergovalinine, α-ergocryptine, β-ergocryptine, ergocristine, ergosinine, β-ergosinine, ergoninine, ergotaminine, ergoptinine, β-ergoptinine, ergocorninine, ergostinine, α-ergocryptinine, β-ergocryptinine, ergocristinine, ergothioneine, ergotinine, ergotoxine, perloline, N-acetylloline, and halostachine wherein the protein of the protein-alkaloid conjugate is selected from the group consisting of bovine serum albumin and ovalbumin, and wherein the conjugate is a carbodiimide reaction product in which said alkaloid is coupled to said protein.

5. The vaccine of claim 4 wherein the alkaloid is ergonovine and the protein is ovalbumin.

6. The vaccine of claim 4 wherein the alkaloid is ergonovine.

\* \* \* \* \*

UNITED STATES PATENT AND TRADEMARK OFFICE
CERTIFICATE OF CORRECTION

PATENT NO. : 5,468,486
DATED : Nov. 21, 1995
INVENTOR(S) : Reddick et al.

It is certified that error appears in the above-indentified patent and that said Letters Patent is hereby corrected as shown below:

Column 2, line 11, change "βergosi-" to
--- β-ergosi- ---
Column 2, line 12, change "βergoptinine" to
--- β-ergoptinine ---
Column 2, line 13, change "βergocrypti-" to
--- β-ergocrypti- ---
Column 2, line 56, change "βergosine" to
--- β-ergosine ---
Column 2, line 59, delete "β-ergostinine" and replace
with --- β-ergoptinine ---
Column 3, line 9, change ".preparation" to
--- preparation ---

Signed and Sealed this

Twenty-third Day of April, 1996

Attest:

BRUCE LEHMAN

Attesting Officer        Commissioner of Patents and Trademarks